US007652100B2

(12) United States Patent
L'Alloret

(10) Patent No.: US 7,652,100 B2
(45) Date of Patent: *Jan. 26, 2010

(54) DISPERSIONS STABILIZED AT TEMPERATURES OF FROM 4 TO 50 DEGREES CELSIUS BY MEANS OF A POLYMER COMPRISING WATER-SOLUBLE UNITS AND UNITS WITH AN LCST

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/069,981

(22) PCT Filed: Jan. 11, 2002

(86) PCT No.: PCT/FR02/00101

§ 371 (c)(1),
(2), (4) Date: Mar. 14, 2002

(87) PCT Pub. No.: WO02/055607

PCT Pub. Date: Jul. 18, 2002

(65) Prior Publication Data
US 2003/0004258 A1     Jan. 2, 2003

(30) Foreign Application Priority Data
Jan. 15, 2001    (FR) .................................. 01 00478

(51) Int. Cl.
     *C08L 101/00*    (2006.01)
(52) U.S. Cl. .................... 524/800; 524/801; 524/804
(58) Field of Classification Search .............. 524/800, 524/801, 804
     See application file for complete search history.

(56) References Cited

U.S. PATENT DOCUMENTS

| 4,274,977 A | * | 6/1981 | Koerner et al. ............. 516/117 |
| 4,559,226 A | * | 12/1985 | Fogel et al. .................... 424/66 |
| 4,737,265 A | * | 4/1988 | Merchant et al. ............ 208/188 |
| 4,839,167 A | * | 6/1989 | Yamamoto et al. ........ 424/70.12 |
| 5,338,352 A | * | 8/1994 | Breneman et al. ........... 106/285 |
| 5,509,913 A | | 4/1996 | Yeo |
| 5,730,966 A | | 3/1998 | Torgerson et al. |
| 5,939,485 A | | 8/1999 | Bromberg et al. |
| 5,939,584 A | | 8/1999 | Merkle et al. |
| 6,001,367 A | | 12/1999 | Bazin et al. |
| 6,159,457 A | | 12/2000 | Mougin |
| 6,998,426 B2 | | 2/2006 | L'alloret et al. |
| 2002/0197231 A1 | | 12/2002 | L'alloret et al. |
| 2003/0031643 A1 | | 2/2003 | L'alloret et al. |
| 2003/0147832 A1 | | 8/2003 | L'alloret et al. |

FOREIGN PATENT DOCUMENTS

| EP | 0 583 814 | | 2/1994 |
| EP | 583814 A1 | * | 2/1994 |
| EP | 0 629 649 | | 12/1994 |
| EP | 629649 A1 | * | 12/1994 |
| EP | 0 754 446 | | 1/1997 |
| EP | 0 987 016 | | 3/2000 |
| EP | 0 998 905 | | 5/2000 |
| EP | 1 043 345 | | 10/2000 |
| EP | 1 046 388 | | 10/2000 |
| EP | 1055694 A2 | * | 11/2000 |
| JP | 61245835 A | * | 11/1986 |
| JP | 2-295912 | | 12/1990 |
| WO | 95/24430 | | 9/1994 |
| WO | 95 24430 | | 9/1995 |
| WO | 97/00275 | | 1/1997 |
| WO | 97 00275 | | 1/1997 |
| WO | 98 29487 | | 7/1998 |
| WO | WO 98/29091 | | 7/1998 |
| WO | WO 98/29092 | | 7/1998 |
| WO | 98/48768 | | 11/1998 |
| WO | 98/50005 | | 11/1998 |
| WO | 99 27924 | | 6/1999 |
| WO | WO 00/35961 | | 6/2000 |
| WO | WO 0035961 A1 | * | 6/2000 |

OTHER PUBLICATIONS

Hourdet et al., Synthesis of the thermoassociative copolymers Polymer, vol. 38 No. 10, pp. 2535-2547 (1997).*
A. Durand et al.: "Synthesis and thermoassociative properties in aqueous solution of graft copolymers containing poly(N-isopropylacrylamide) side chains" Polymer, vol. 40, No. 17, pp. 4941-4951 Aug. 1999.
D. Hourdet et al.: "Reversible thermothickening of aqueous polymer solutions" Polymer, vol. 35, No. 12, pp. 2624-2630 1994.
F. L'Alloret et al.: "Aqueous solution behavior of new thermoassociative polymers" Colloid and Polymer Science, vol. 273, No. 12, pp. 1163-1173 1995.
F. L'Alloret et al: "Reversible thermoassociation of water-soluble polymers" Revue De L'Institut Francais Du Petrole, vol. 52, No. 2, pp. 117-128 1997.
F.E. Bailey, Jr., et al: "Some properties of poly(ethylene oxide) in aqueous solution" *Journal of Applied Polymer Science*, vol. 1, No. 1, pp. 56-62 (1959).

(Continued)

*Primary Examiner*—Kelechi C Egwim
(74) *Attorney, Agent, or Firm*—Oblon, Spivak, McClelland, Maier & Neustadt, L.L.P.

(57) ABSTRACT

Cosmetic dispersions comprising an aqueous phase and an oily phase, the aqueous phase containing a polymer comprising water-soluble units and units with an LCST, wherein the LCST units an have in water a demixing temperature of from 5 to 40° C. for a concentration of 1% by mass is used, the polymer being present in a concentration such that the gel point of the aqueous phase is from 5 to 40° C., to ensure the stability of the dispersions at temperatures from 4° C. to 50° C.

23 Claims, 1 Drawing Sheet

OTHER PUBLICATIONS

M. Heskins, et al.: "Solution properties of Poly(N-isopropylacrylamide)" *J. Macromol.Sci. Chem.*, vol. A2 No. 8, pp. 1441-1455 Dec. 1968.

D. Hourdet, et al.: "Synthesis of the thermoassociative copolymers" *Polymer*, vol. 38 No. 10, pp. 2535-2547 (1997).

Lloyd D. Taylor, et al.: "Preparation of films exhibiting a balanced temperature dependence to permeation by aqueous solutions—a study of lower consolute behavior" *Journal of Polymer Science*, vol. 13, pp. 2551-2570 (1975).

D. Hourdet et al., Polymer, 1994, vol. 35, No. 12, pp. 22624-2630.

F. L'Alloret et al., Coll. Polym. Sc., 1995, vol. 273, No. 12, pp. 1163-1773.

F. L'Alloret et al., Revue de l'Institut Francais du Petrole (Review of the French Petroleum Institute), 1997, vol. 52, No. 2, pp. 117-128.

\* cited by examiner

DISPERSIONS STABILIZED AT TEMPERATURES OF FROM 4 TO 50 DEGREES CELSIUS BY MEANS OF A POLYMER COMPRISING WATER-SOLUBLE UNITS AND UNITS WITH AN LCST

TECHNICAL FIELD

The present invention relates to dispersions, especially cosmetic dispersions, comprising at least one aqueous phase and at least one oily phase. Such dispersions may be in the form of an oil-in-water emulsion, in the form of a water-in-oil-in-water multiple emulsion, or alternatively in the form of a multiphase composition consisting of a dispersion of mineral and/or organic particles in the aqueous phase of an oil-in-water emulsion.

The invention relates more particularly to the stabilization of such dispersions over a wide range of temperatures ranging from 4 to 50° C., without harming their properties.

In the cosmetic field, it is essential for a dispersion such as a suspension or an emulsion to be stable over a wide temperature range. The reason for this is that, during its lifetime, the cosmetic dispersion may be exposed to temperatures ranging from 4° C. to a minimum +50° C. depending on the climatic, storage and/or transportation conditions. For example, it is necessary for a cream that is transported in a car which could spend a long time in the sunshine, that is to say at a temperature readily reaching 50° C., to conserve its stability. It is also necessary for these creams to be able to be used in hot countries without any problems arising as regards their transportation and storage. The instability of a dispersion is generally reflected by a macroscopic demixing, resulting in separation into at least two phases.

Moreover, cosmetic compositions must show satisfactory stability in storage cycles. A storage cycle consists in passing the composition through several successive temperatures. Thus, the composition is maintained for a certain period (for example for 6 hours) at room temperature (about +20° C.), then over the same period (i.e. 6 hours) the temperature is reduced to about 4° C., the composition is then left at this temperature of 4° C. for the same period of time again (i.e. 6 hours) and the temperature is then raised to room temperature (+20° C.) over the same period of time (6 hours), and this is repeated several times (generally 5 times) This passage through various temperatures makes it possible to test the satisfactory stability of a composition. Now, it is advantageous for cosmetic compositions to have excellent stability, irrespective of the conditions under which they are found.

In the case of cosmetic dispersions consisting of oil-in-water emulsions, water-in-oil-in-water multiple emulsions, and dispersions of mineral and/or organic particles in the aqueous phase of an oil-in-water emulsion, the stability of these dispersions is generally weakened when the temperature increases, on account of the fall in viscosity of the aqueous phase. This is reflected by a phenomenon of sedimentation when the dispersed phase has a density greater than that of the continuous aqueous phase; this is the case for many aqueous suspensions of mineral particles. When the dispersed phase is less dense than the continuous aqueous phase, a phenomenon of creaming takes place, such as, for example, in the case of emulsions.

PRIOR ART

In order to ensure the stability of such dispersions for temperatures ranging from 4 to 50° C., use has been made of aqueous-phase gelling agents such as crosslinked polyacrylic acid derivatives (Carbopols sold by Goodrich) and natural polymers such as xanthan gum (Keltrol T sold by Kelco). The use of such gelling agents limits the range of textures available to the gelled formations.

It would therefore be necessary to be able to use other compounds making it possible, on the one hand, to ensure the stability of cosmetic dispersions at temperatures from 4° C. to 50° C. and, on the other hand, to maintain a wide range of textures available at room temperature, with fluid or gelled formulations.

DESCRIPTION OF THE INVENTION

One subject of the present invention is, precisely, the use of a polymer comprising water-soluble units and units with an LCST, added to the aqueous phase of such dispersions, to ensure the stability of these dispersions when they are subjected to temperature variations in the range from 4 to 50° C.

Thus, a subject of the present invention is a dispersion comprising at least one aqueous phase and at least one oily phase, characterized in that the aqueous phase comprises a polymer comprising water-soluble units and units with an LCST, the units with an LCST having in water a demixing temperature of from 5 to 40° C. at a concentration of 1% by mass, and the polymer being present in the aqueous phase at a concentration such that the gel point of the aqueous phase is from 5 to 40° C. and preferably from 10 to 35° C., to ensure the stability of the dispersion when it is subjected to temperature variations in the range from 4 to 50° C.

According to the invention, the dispersion may be formed by an oil-in-water (O/W) emulsion in which water is the aqueous phase, by a water-in-oil-in-water (W/O/W) multiple emulsion, or alternatively by a dispersion of mineral and/or organic particles in the aqueous phase of an oil-in-water emulsion.

Polymers comprising water-soluble units and units with an LCST have been described in the following documents: D. Hourdet et al., Polymer, 1994, Vol. 35, No. 12, pages 2624 to 2630 [1]; F. L'Alloret et al., Coll. Polym. Sci., 1995, Vol. 273, No. 12, pages 1163-1173 [2]; F. L'Alloret et al., Revue de l'Institut Français du Pétrole, 1997, Vol. 52, No. 2, pages 117-128 [3]; EP-A-0 583 814 [4] and EP-A-0 629 649 [5].

As described in these documents, these polymers comprise water-soluble units and units with an LCST, which have in water a lower critical solution temperature. Thus, these units with an LCST are units whose solubility in water is modified beyond a certain temperature. They are units having a heat-induced demixing temperature (or cloud point) defining their region of water solubility. The minimum demixing temperature obtained as a function of the polymer concentration is known as the "LCST" (Lower Critical Solution Temperature). For each polymer concentration, a heat-induced demixing temperature is observed; it is higher than the LCST, which is the minimum point of the curve. Below this temperature, the polymer is water-soluble, and above this temperature, the polymer loses its water solubility.

Thus, these polymers have water-gelling properties brought about by increasing the temperature. These properties may be exploited for uses in the petroleum field, as described in documents [4] and [5].

WO-A-95/24430 [6] also describes copolymers comprising units with an LCST and pH-sensitive units, which have heat-induced gelling properties. For use for the controlled release of active principles in the pharmaceutical field and in the cosmetic field. The gels obtained are opaque and have an LCST, unlike the polymers of the invention which comprise chains with an LCST but whose overall behaviour is not of LCST type and which lead to transparent compositions.

According to the invention, a polymer is chosen whose units with an LCST have a demixing temperature of from 5 to 40° C. at a concentration of 1% by mass, so as to obtain the gelation of an aqueous phase containing this polymer in the desired range. Furthermore, the polymer concentration used is sufficient to allow interactions between units with an LCST borne by different macromolecules, and to obtain this gelation of the aqueous phase, thus making it possible to ensure the stability of the dispersion.

In the case of cosmetic dispersions in which the desired texture is obtained by means of a standard gelling agent, when the temperature increases, the gelling agent used at the start becomes fluidized. According to the invention, by virtue of the presence of the polymer comprising water-soluble units and units with an LCST, this heat-induced reduction in viscosity does not take place.

These gelling properties are observed when the polymer concentration is sufficient to allow interactions between units with an LCST borne by different macromolecules. The minimum concentration required, known as the "critical aggregation concentration", or CAC, is evaluated by Theological measurements: it is the concentration at and above which the viscosity of an aqueous solution of a polymer the invention becomes higher than the viscosity of a solution of the equivalent polymer not comprising chains with an LCST.

Beyond the CAC, the polymers of the invention have gelling properties when the temperature becomes higher than a critical value, known as the "gel point", or $T_{gel}$. According to the literature data, there is good agreement between the $T_{gel}$ and the demixing temperature of the chains with an LCST, under the same concentration conditions. The gel point of an aqueous solution of a polymer of the invention is determined by rheological measurements: it is the temperature at and above which the viscosity of the polymer solution becomes higher than the viscosity of the solution of the equivalent polymer not comprising LCST units.

The polymers used in the invention are characterized by a gel point ranging from 5° C. to 40° C. and preferably from 10° C. to 35° C. for a concentration in water equal to 2% by mass.

U.S. Pat. No. 5,939,485 [7] and WO 97/00275 [8] describe reversible-gelling polymer systems comprising a sensitive component capable of aggregating in response to a change in an external stimulus and a structural component. The external stimulus may be the temperature. The sensitive component may be a block copolymer such as a Poloxamer, for example a Pluronic®, which aggregates microscopically beyond a critical temperature not corresponding to an LCST. A non-ionic surfactant may also be used as a sensitive component. These polymers have heat-induced gelling properties and may be used in the pharmaceutical field to deliver medicinal products and in many other fields including the cosmetics field.

In these formulations, the sensitive component of the polymer system has a different behaviour from that of units with an LCST during heating. Thus, when it is heated to about 30-40° C., it exhibits a temperature of micellization, that is to say an aggregation at the microscopic level, and then, when it is heated further, a higher LCST temperature. This LCST corresponds to a macroscopic aggregation between the molecules. It is explained in WO-A-97/00275 [8] on pages 16 and 17 that the gelation and the LCST are observed at temperatures that differ by about 70° C. This shows that these polymers are different from the polymers of the present invention.

Document WO-A-98/48768 [9] also discloses cosmetic compositions using a reversible heat-induced gelling polymer system, comprising polyacrylic acid and a poloxamer. This polymer is thus different from the polymers of the invention.

The systems with reversible gelation described in documents [7], [8] and [9] are different from the polymer systems used in the invention. Firstly, the heat-sensitive units do not have a demixing temperature in the range from 5 to 40° C. Secondly, unlike the polymers used in the invention, in which the demixing temperature of the chains with an LCST corresponds substantially to the gel point under the same concentration conditions, the heat sensitive units of these polymers have a demixing temperature that is very far from the gel point.

Furthermore, it was not envisaged to use these polymer systems to stabilize dispersions such as suspensions and emulsions, subjected to temperature variations in the range from 4 to 50° C.

The polymers used in the invention may be block polymers or grafted polymers, which comprise, on the one hand, water-soluble units and, on the other hand, units with an LCST as defined above.

The polymers used in the context of the invention may thus be block polymers comprising, for example, water-soluble blocks alternating with blocks with an LCST.

These polymers may also be in the form of grafted polymers whose backbone is formed from water-soluble units, bearing grafts with an LCST. This structure may be partially crosslinked.

It is pointed out that, in the present text, the terms "water-soluble unit" and "LCST unit" do not include the group linking together, on the one hand, the water-soluble units and, on the other hand, the units with an LCST, the linking units being derived from the reaction of the reactive sites borne, on the one hand, by water-soluble units and, on the other hand, by units with an LCST.

Water-soluble units in these polymers are units that are soluble in water at a temperature of from 5° C. to 80° C., to a proportion of at least 10 g/l and preferably at least 20 g/l.

However, the term "water-soluble units" also means units not necessarily having the solubility mentioned above, but which in aqueous solution at 1% by weight, from 5° C. to 80° C., allow the production of a solution that is macroscopically homogeneous and transparent, that is to say having a maximum light transmittance value, irrespective of the wavelength between 400 and 800 nm, through a sample 1 cm thick, of at least 85% and preferably of at least 90%.

These water-soluble units do not have a heat-induced demixing temperature of LCST type.

These water-soluble units may be obtained by free-radical polymerization of vinyl monomers, or by polycondensation, or alternatively may consist of natural polymers or modified existing natural polymers.

By way of example, mention may be made of the following monomers, which may be used to form the said water-soluble units, alone or as a mixture:

(meth)acrylic acid;

vinyl monomers of formula (I) below:

in which:
R is chosen from H, —CH$_3$, —C$_2$H$_5$ or —C$_3$H$_7$, and
X is chosen from:
  alkyl oxides of —OR' type in which R' is a linear or branched, saturated or unsaturated hydrocarbon radical containing from 1 to 6 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R'+R_1+R_2+R_3$ does not exceed 7; and —$NH_2$, —$NHR_4$ and —$NR_4R_5$ groups in which $R_4$ and $R_5$ are, independently of each other, linear or branched, saturated or unsaturated hydrocarbon radicals containing 1 to 6 carbon atoms, with the proviso that the total number of carbon atoms in $R_4+R_5$ does not exceed 7, the said $R_4$ and $R_5$ optionally being substituted with a halogen atom (iodine, bromine, chlorine or fluorine); a hydroxyl (—OH); sulphonic (—$SO_3^-$), sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R_4+R_5+R_1+R_2+R_3$ does not exceed 7;

maleic anhydride;

itaconic acid;

vinyl alcohol of formula $CH_2$=CHOH;

vinyl acetate of formula $CH_2$=CH—$OCOCH_3$;

N-vinyllactams such as N-vinylpyrrolidone, N-vinyl caprolactam and N-butyrolactam;

vinyl ethers of formula $CH_2$=$CHOR_6$ in which $R_6$ is a linear or branched, saturated or unsaturated hydrocarbon radical containing from 1 to 6 carbons;

water-soluble styrene derivatives, especially styrene sulphonate;

dimethyldiallylammonium chloride; and vinylacetamide.

Among the polycondensates and the natural polymers or modified natural polymers that may constitute all or part of the water-soluble units, mention may be made of:

water-soluble polyurethanes;

xanthan gum, especially the product sold under the names Keltrol T and Keltrol SF by Kelco; or Rhodigel SM and Rhodigel 200 from Rhodia;

alginates (Kelcosol from Monsanto) and derivatives thereof such as propylene glycol alginate (Kelcoloid LVF from Kelco);

cellulose derivatives and especially carboxymethylcellulose (Aquasorb A500, Hercules), hydroxypropylcellulose, hydroxyethylcellulose and quaternized hydroxyethylcellulose;

galactomannans and derivatives thereof, such as konjac gum, guar gum, hydroxypropylguar, hydroxypropylguar modified with sodium methylcarboxylate groups (Jaguar XC97-1, Rhodia), hydroxypropyltrimethylammonium guar chloride.

Mention may also be made of polyethyleneimine.

The water-soluble units preferably have a molar mass ranging from 1000 g/mol to 5 000 000 g/mol when they constitute the water-soluble backbone of a grafted polymer.

These water-soluble units preferably have a molar mass ranging from 500 g/mol to 100 000 g/mol when they constitute a block of a multiblock polymer.

The units with an LCST of the polymers used in the invention may be defined as being units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, a heat-induced demixing temperature is observed; it is higher than the LCST, which is the minimum point of the curve. Below this temperature, the polymer is soluble in water; above this temperature, the polymer loses its solubility in water.

The expression "soluble in water at a temperature T" means that the units have a solubility at T of at least 1 g/l and preferably of at least 2 g/l.

The measurement of the LCST may be performed visually: the temperature at which the cloud point of the aqueous solution appears is determined; this cloud point is reflected by the opacification of the solution, or the loss of transparency.

In general, a transparent composition will have a maximum light transmittance value, irrespective of the wavelength between 400 and 800 mm, through a sample 1 cm thick, of at least 85% and preferably of at least 90%.

The transmittance may be measured by placing a sample 1 cm thick in the light beam of a spectrophotometer working at the wavelengths of the light spectrum.

The units with an LCST in the polymers used in the invention may consist of one or more of the following polymers:

polyethers such as polyethylene oxide (PEO), polypropylene oxide (PPO) or random copolymers of ethylene oxide (EO) and of propylene oxide (PO), polyvinyl methyl ether, poly-N-isopropylacrylamide and poly-N-ethylacrylamide, and polyvinylcaprolactam.

Preferably, the units with an LCST consist of polypropylene oxide $(PPO)_n$ with n=1 to 50, or random copolymers of ethylene oxide (EO) and of propylene oxide (PO), represented by the formula:

$$(EO)_m(PO)_n$$

in which m is an integer ranging from 1 to 40 and preferably from 2 to 20, and n is an integer ranging from 10 to 60 and preferably from 20 to 50.

Preferably, the molar mass of these units with an LCST is from 500 to 5300 g/mol and especially from 1500 to 4000 g/mol.

It has been found that the random distribution of the EO and PO units is reflected by the existence of a lower critical demixing temperature, beyond which a macroscopic phase separation is observed. This behaviour is different from that of block (EO)(PO) copolymers, which form micelles beyond a critical temperature known as the micellization temperature (macroscopic aggregation).

The units with an LCST may thus especially be derived from aminated, especially monoamino, diamino or triamino, random copolymers of ethylene oxide and of propylene oxide. Among the commercially available units with an LCST that may be mentioned are the copolymers sold under the name Jeffamine by Huntsman, and especially Jeffamine XTJ-507 (M-2005), Jeffamine D-2000 and Jeffamine XTJ-509 (or T-3000).

The units with an LCST may also be derived from random EO/PO copolymers containing OH end groups, such as those sold under the name Polyglycols P41 and B11 by Clariant.

Polymeric and copolymeric N-substituted acrylamide derivatives having an LCST, and also polyvinylcaprolactam and vinylcaprolactam copolymers may also be used in the invention as units with an LCST.

As examples of polymeric and copolymeric N-substituted acrylamide derivatives having an LCST, mention may be made of poly-N-isopropylacrylamide, poly-N-ethylacrylamide and copolymers of N-isopropylacrylamide (or of N-ethylacrylamide) and of a vinyl monomer having the formula (I) given above, or of a monomer chosen from maleic anhydride, itaconic acid, vinylpyrrolidone, styrene and its derivatives, dimethyldiallylammonium chloride, vinylacetamide, vinyl ethers and vinyl acetate derivatives.

The molar mass of these polymers is preferably from 1000 g/mol to 500 000 g/mol and preferably from 2000 to 50 000 g/mol. These polymers may be synthesized by free-radical polymerization using a pair of initiators such as aminoethanethiol hydrochloride, in the presence of potassium persulphate, so as to obtain precursor oligomers with a reactive amino end group.

As examples of vinylcaprolactam copolymers, mention may be made of copolymers of vinylcaprolactam and of a vinyl monomer of formula (I) given above, or of a monomer chosen from maleic anhydride, itaconic acid, vinylpyrrolidone, styrene and its derivatives, dimethyldiallylammonium chloride, vinylacetamide, vinyl alcohol, vinyl acetate, vinyl ethers and vinyl acetate derivatives.

The molar mass of these vinylcaprolactam polymers or copolymers is generally from 1000 g/mol to 500 000 g/mol and preferably from 2000 to 50 000 g/mol.

These compounds may be synthesized by free-radical polymerization using a pair of initiators such as aminoethanethiol hydrochloride, in the presence of potassium persulphate, so as to obtain precursor oligomers with a reactive amino end group.

The proportion by mass of units with an LCST in the final polymer is preferably from 5% to 70%, especially from 20% to 65% and particularly from 30% to 60% by weight relative to the final polymer.

As defined above, the demixing temperature of the said units with an LCST is from 5° C. to 40° C. and preferably from 10° C. to 35° C., for a concentration in water of 1% by mass of the said units with an LCST.

The polymers used in the context of the invention may be readily prepared by a person skilled in the art on the basis of his general knowledge, using grafting, copolymerization or coupling reaction processes.

When the final polymer is in the form of a grafted polymer, especially having a water-soluble backbone with LCST side chains, it is possible to prepare it by grafting units with an LCST containing at least one reactive end group, especially an amino end group, onto a water-soluble polymer forming the backbone, bearing at least 10% (on a molar basis) of reactive groups such as carboxylic acid functions. This reaction may be carried out in the presence of a carbodiimide such as dicyclohexylcarbodiimide or 1-(3-dimethylaminopropyl)-3-ethylcarbodiimide hydrochloride, in a solvent such as N-methylpyrrolidone or water.

Another possibility for preparing grafted polymers consists in copolymerizing, for example, a macromonomer with an LCST (chain with an LCST described above with a vinyl end group) and a water-soluble vinyl monomer such as acrylic acid or vinyl monomers of formula (I).

When the final polymer is in the form of a block polymer, it is possible to prepare it by coupling between water-soluble units and units with an LCST, these units having complementary reactive sites at each end.

In the case of grafting processes and coupling processes, the reactive sites of the units with an LCST may be amine functions, especially monoamines, diamines or triamines, and OH functions. In this case, the reactive sites of the water-soluble units may be carboxylic acid functions.

As has been seen previously, the dispersions of the invention may be in the form of oil-in-water emulsions and water-in-oil-in-water multiple emulsions, or in the form of a multiphase composition consisting of a dispersion of particles in the aqueous phase of an O/W emulsion. In all cases, the stability of the dispersions is ensured by the presence of the polymer containing water-soluble units and units with an LCST described above. To ensure this stability, the concentration by mass of the polymer in the continuous aqueous phase of the oil-in-water emulsions and of the water-in-oil-in-water emulsions or of the multiphase compositions, is generally from 0.01% to 20% and preferably from 0.1% to 10%.

The continuous aqueous phase may consist of a physiologically acceptable medium allowing a topical application, and especially a cosmetic application.

In the present patent application, the expression "physiologically acceptable medium" means a medium that is compatible with all keratin materials such as the skin, including the scalp, the nails, mucous membranes, the eyes and the hair, or any other area of body skin.

The physiologically acceptable medium for the dispersions of the invention comprises water. The amount of water may range from 30 to 99.98% by weight and preferably from 40 to 95% by weight relative to the total weight of the composition.

The water used may be, besides water, a floral water such as cornflower water, a mineral water such as eau de Vittel, eau de Lucas or eau de la Roche Posay and/or a spring water.

The physiologically acceptable medium may contain, besides water, one or more solvents chosen from lower alcohols containing from 1 to 8 carbon atoms, such as ethanol; polyols such as glycerol; glycols, for instance butylene glycol, isoprene glycol, propylene glycol, polyethylene glycols such as PEG-8; sorbitol; sugars such as glucose, fructose, maltose, lactose and sucrose; and mixtures thereof. The amount of solvent(s) may range from 0.5 to 30% by weight and preferably from 5 to 20% by weight relative to the total weight of the aqueous phase.

The oily phase preferably comprises at least one oil.

As oils which can be used in the composition of the invention, mention may be made for example of:

hydrocarbon-based oils of animal origin, such as perhydrosqualene;

hydrocarbon-based oils of plant origin, such as liquid triglycerides of fatty acids of 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or karite butter;

synthetic esters and ethers, in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, petroleum jelly, polydecenes or hydrogenated polyisobutene such as parleam oil;

natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;

fatty alcohols containing from 8 to 26 carbon atoms, such as cetyl alcohol, stearyl alcohol, and the mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils such as those described in document JP-A-2-295 912;

silicone oils such as volatile or non-volatile polydimethylsiloxanes (PDMSs) containing a linear or cyclic silicone chain, which are liquid or pasty at room temperature, in particular cyclopolydimethylsiloxanes (cyclomethicones) such as cyclohexasiloxane; polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

The term "hydrocarbon-based oil" in the list of abovementioned oils embraces any oil comprising predominantly carbon and hydrogen atoms, and optionally ester, ether, fluoro, carboxylic acid and/or alcohol groups.

The other fatty substances which may be present in the oily phase are, for example, fatty acids containing from 8 to 30 carbon atoms, for instance stearic acid, lauric acid, palmitic acid and oleic acid; waxes, for example lanolin, beeswax, carnauba wax, candelilla wax, paraffin wax, lignite wax or microcrystalline waxes, ceresine or ozokerite, synthetic waxes, for instance polyethylene waxes and Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art in order to prepare a composition having the desired properties, for example consistency or texture properties.

The amount of oily phase may range, for example, from 0.01% to 50% by weight and preferably from 0.1% to 30% by weight relative to the total weight of the composition.

The dispersions of the invention may also contain adjuvants commonly used in cosmetics and dermatology, especially for uses in the fields of care, make-up, make-up removal, antisun products, hair products and shaving products. These adjuvants may consist of mineral or organic fillers, surfactants, hydrophilic or lipophilic active agents, preserving agents, gelling agents, plasticizers, antioxidants, fragrances, odour absorbers, antifoams, sequestering agents (EDTA), acidic or basic pH adjusters or buffers, and dyestuffs (pigments or colorants or nacres). Depending on their nature, these adjuvants may be introduced into the oily phase, into the aqueous phase and/or into lipid vesicules. The amounts of these various adjuvants are those conventionally used in the fields under consideration, and, for example, from 0.01 to 20% of the total weight of the dispersion. Needless to say, a person skilled in the art will take care to select the optional compound(s) to be added to the dispersions of the invention such that the advantageous properties intrinsically associated with these dispersions are not, or are not substantially, adversely affected by the addition envisaged.

The expression "mineral or organic particles" should be understood as comprising fillers, pigments and nacres. The term "fillers" should be understood as meaning colourless or white, mineral or synthetic, lamellar or non-lamellar particles intended to give body or rigidity to the composition and/or softness, a matt effect and uniformity to make-up. Fillers that may especially be mentioned are talc, mica, silica, boron nitride, bismuth oxychloride, kaolin, Nylon powders such as Nylon-12 (Orgasol sold by the company Atochem), polyethylene powders, Teflon (tetrafluoroethylene polymer powders), polyurethane powders, polystyrene powders, polyester powders, optionally modified starch, copolymer microspheres, such as those sold under the name Expancel by the company Nobel Industrie, microsponges, for instance Polytrap sold by the company Dow Corning, silicone resin microbeads such as those sold by the company Toshiba under the name Tospearl, precipitated calcium carbonate, magnesium carbonate, magnesium hydrocarbonate, hydroxyapatite, hollow silica microspheres (Silica Beads from the company Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate, and mixtures thereof.

The term "pigments" should be understood as meaning white or coloured, mineral or organic particles, insoluble in the medium, that are intended to colour and/or opacify the composition. They may be white or coloured, mineral and/or organic, and of standard or nanometric size. Among the mineral pigments and nanopigments that may be mentioned are titanium dioxide, zirconium dioxide or cerium dioxide, and also zinc oxide, iron oxide or chromium oxide, nanotitaniums (titanium dioxide nanopigments), nanozincs (zinc oxide nanopigments) and ferric blue. Among the organic pigments that may be mentioned are carbon black and lakes, for instance calcium, barium, aluminium or zirconium salts, or acidic dyes such as halo acid dyes, azo dyes or anthraquinone dyes.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also coloured titanium mica.

A gelling agent may also be added to the compositions of the invention so as to adjust the texture of the emulsion and to gain access to a wide range of textures from a milk to a cream.

The gelling agents that may be used may be hydrophilic gelling agents. Examples of hydrophilic gelling agents that may be mentioned in particular are carboxyvinyl polymers (carbomer), acrylic copolymers such as acrylate/alkylacrylate copolymers, polyacrylamides, polysaccharides, natural gums and clays.

The surfactants that may be used in the oil-in-water emulsions may in particular be nonionic emulsifying surfactants, for example the products of addition of from 1 to 200 mol of ethylene oxide or of propylene oxide to partial esters of polyols containing 2 to 16 carbon atoms and of fatty acids containing 12 to 22 carbon atoms, for instance fatty acid esters of polyethylene glycol such as PEG-100 stearate, PEG-50 stearate and PEG-40 stearate; fatty acid esters of polyols such as glyceryl stearate, sorbitan tristearate and oxyethylenated sorbitan stearates sold under the trade names Tween® 20 or Tween® 60, sugar esters, for instance sucrose stearate and mixtures thereof.

The dispersions of the invention may especially be in the form of a cosmetic make-up or care composition, which may be applied to the skin, including the scalp, the nails, the hair, the eyelashes, the eyebrows, the eyes, mucous membranes and semi-mucous membranes, and any other area of body or facial skin.

The dispersions according to the invention may be used in many cosmetic or dermatological applications; they may especially be used for treating, caring for and/or making up facial skin and/or body skin, mucous membranes (lips), the scalp and/or keratin fibres (hair or eyelashes).

Thus, the dispersions of the invention may be used as care products and/or hygiene products such as protective, treatment or care creams for the face, for the hands or for the body, protective or care body milks, lotions, milks, gels or mousses to care for the skin and mucous membranes or to cleanse, remove make-up from or scrub the skin. They may also constitute make-up products for keratin fibres, for the skin, for the lips and/or for the nails, for instance a foundation, a face powder, an eyeshadow, a lipstick, a mascara or an eyeliner.

The compositions of the invention may also be used as antisun products for protecting the skin against UV rays.

Thus, a subject of the present invention is the cosmetic use of the dispersion as defined above, to treat, care for and/or make up facial skin and/or body skin, mucous membranes (lips), the scalp and/or keratin fibres.

Another subject of the invention is a cosmetic process for treating human keratin materials such as the skin, including the scalp, the hair, the eyelashes, the eyebrows, the nails or mucous membranes, especially the lips, characterized in that a dispersion as defined above is applied to the keratin materials, according to the usual technique for using this composition. For example: application of creams, gels, sera, lotions or milks to the skin, the scalp and/or mucous membranes.

Other characteristics and advantages of the invention will emerge more clearly on reading the description which follows, which is given by way of non-limiting illustration, with reference to the attached drawing.

DETAILED DESCRIPTION OF THE EMBODIMENTS

Figure 1:
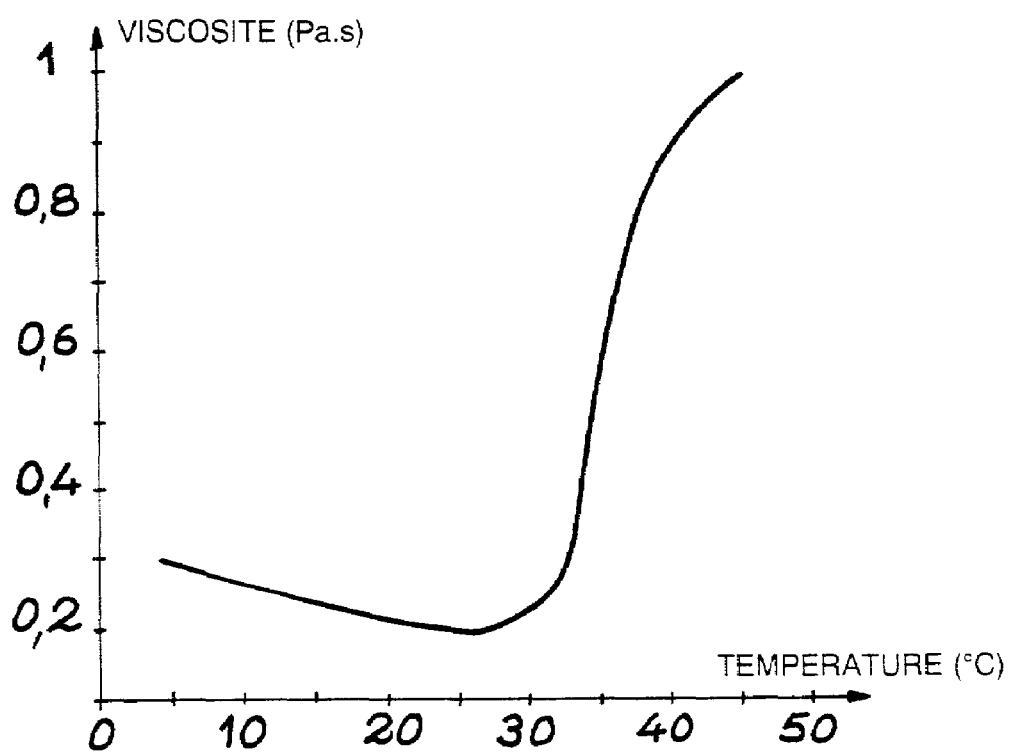
FIG. 1 illustrates the change in viscosity (in Pa.s) of solutions of Polymer 2 used in the invention as a function of the temperature (in ° C.).

The examples that follow illustrate the use of polymers comprising water-soluble units and units with an LCST for preparing temperature-stable dispersions.

The polymers used in these examples consist of a polyacrylic acid (PAA) backbone bearing side chains or grafts with an LCST. They are characterized by the molar mass of the water-soluble backbone (polyacrylic acid), the chemical nature of the chains with an LCST, their proportion by mass in the polymer and their molar mass.

The characteristics of the polymers used are given in Table 1.

TABLE 1

| | Water-soluble backbone | Grafts (units with an LCST) | Proportion: units with an LCST in the final polymer (by weight) | Degree of grafting (mol %) |
|---|---|---|---|---|
| Polymer 1 | Polyacrylic acid; MW = 450 000 | $(EO)_6(PO)_{39}$ random Jeffamine M-2005; MW = 2600 | 51% | 3.9% |
| Polymer 2 | Polyacrylic acid; MW = 550 000 | Poly-N-isopropyl-acrylamide (pNIPAM) MW-10 000 | 49% | 0.9% |

These polymers are prepared in the following manner.

Preparation of Polymer 1

3 grams of polyacrylic acid with an average molar mass of 450 000 g/mol (Aldrich) are dissolved in 220 ml of N-methylpyrrolidone in a 500 ml reactor equipped with a condenser, with stirring at 60° C. for 12 hours. 4.181 grams of monoamino random $(EO)_6$ $(PO)_{39}$ copolymer with a molar mass of 2600 g/mol having a cloud point, at a concentration of 1% by weight in water, of 16° C. (Jeffamine M-2005 from Huntsman) are dissolved in 50 ml of N-methylpyrrolidone with stirring, at 20° C., for 15 minutes. The solution obtained is added dropwise to the reaction medium containing the polyacrylic acid, with vigorous stirring at 60° C.

2.158 grams of dicyclohexylcarbodiimide are dissolved in 30 ml of N-methylpyrrolidone with stirring at 20° C. for 15 minutes. The solution obtained is added dropwise to the reaction medium containing the polyacrylic acid and the monoamino random $(EO)_6$ $(20)_{39}$ copolymer, with vigorous stirring at 60° C. The final mixture is stirred for 12 hours at 60° C.

The mixture is cooled to 20° C. and is then placed in a refrigerator at 4° C. for 24 hours. The crystals of dicyclohexylurea formed are removed by filtration of the reaction medium.

The polymer is then neutralized with 19 g of 35% sodium hydroxide (4-fold excess relative to the number of moles of acrylic acid), leading to its precipitation. After standing for 12 hours, the reaction medium is filtered so as to recover the precipitated polymer. This polymer is dried under vacuum at 35° C. for 24 hours.

13.55 grams of solid are recovered and are dissolved in 2 liters of deionized water. This solution is ultrafiltered using a Millipore ultrafiltration system containing a membrane with a cutoff threshold set at 10 000 daltons. The solution thus purified is freeze-dried so as to collect the polymer in solid form.

7.05 grams of polyacrylic acid (450 000 g/mol) grafted with 3.9% (on a molar basis) of monoamino random $(EO)_6$ $(PO)_{39}$ copolymer are obtained.

The proportion by mass of units with an LCST in the final polymer is 51%.

The polymer thus obtained has a solubility in water, at 20° C., of at least 10 g/l.

Preparation of Polymer 2

Polymer 2, which comprises poly-N-isopropylacrylamide (pNIPAM) grafts, is prepared by a 2-step process:

1) Synthesis of the pNIPAM oligomers bearing a reactive amino end group.

8 grams of N-isopropylacrylamide and 80 ml of dimethyl sulphoxide are introduced into a 250 ml three-necked round-bottomed flask equipped with a condenser and a nitrogen inlet. This mixture is heated with stirring to 29° C. using a water bath and nitrogen is bubbled through. After 45 minutes, 0.161 gram of aminoethanethiol hydrochloride predissolved in 4 ml of dimethyl sulphoxide is added to the reaction medium. 5 minutes later, 0.191 gram of potassium persulphate dissolved in 8 ml of dimethyl sulphoxide is added to the reaction medium. This reaction medium is stirred under a nitrogen atmosphere for 3 hours at 29° C.

The poly-N-isopropylacrylamide (pNIPAM) oligomers synthesized are isolated by precipitation from the reaction medium in a mixture of acetone (40% by volume) and hexane (60%).

2) Grafting of the pNIPAM oligomers onto polyacrylic acid 3 grams of polyacrylic acid with a molar mass of 550 000 g/mol are dissolved in 100 ml of 1-methyl-2-pyrrolidone in a 250 ml three-necked round-bottomed flask, with stirring at 60° C. for 12 hours. 3.757 grams of pNIPAM oligmers predissolved in 25 ml of 1-methyl-2-pyrrolidone are introduced dropwise into the reaction medium with stirring. 15 minutes later, 0.776 gram of dicyclohexylcarbodiimide predissolved in 25 ml of 1-methyl-2-pyrrolidone is introduced dropwise into the reaction medium with vigorous stirring. The reaction medium is maintained at 60° C. for 12 hours with stirring.

The reaction medium is then cooled to 20° C. and then placed in a refrigerator at 4° C. for 24 hours. The dicyclohexylurea crystals formed are then removed by filtration. The polymer is then neutralized using 19 g of 35% sodium hydroxide (4-fold excess relative to the number of moles of acrylic acid), leading to its precipitation. After standing for 12 hours, the reaction medium is filtered so as to recover the precipitated polymer. This polymer is dried under vacuum at 35° C. for 24 hours.

10.2 grams of solid are recovered and are dissolved in 2 liters of deionized water. This solution is ultrafiltered using a Millipore ultrafiltration system containing a membrane with a cutoff threshold set at 10 000 daltons. The solution thus purified is freeze-dried so as to collect the polymer in solid form.

4.8 grams of polyacrylic acid (550 000 g/mol) grafted with 0.9% (on a molar basis) of poly-N-isopropylacrylamide are obtained.

The proportion by mass of units with an LCST in the final polymer is 49%.

The demixing temperatures of the units with an LCST of the polymers, that is to say of the Jeffamine units and of the pNIPAM units, are determined.

These demixing temperatures are determined by visible UV spectroscopy by measuring, at a wavelength equal to 500 nm, the transmittance of aqueous solutions of these units as a function of temperature; the demixing temperature is identified at the temperature beyond which the transmittance becomes 10% less than its value at 10° C. The results obtained for various concentrations by mass are collated in Table 2 below:

TABLE 2

| Concentration by mass in aqueous solution (%) | Random $(EO)_6(PO)_{39}$ Jeffamine M-2005; MW = 2600 | Poly-N-isopropyl-acrylamide pNIPAM MW = 10 000 |
|---|---|---|
| 0.025 | 37° C. | 37° C. |
| 0.05 | 36° C. | 36° C. |
| 0.15 | / | 32° C. |
| 1 | 16° C. | 32° C. |

The critical aggregation concentration (CAC) of polymers 1 and 2 in pure water is determined by rheology. This is the concentration at and above which the viscosity of an aqueous solution of the polymer under consideration becomes higher than the viscosity of a solution of the equivalent polymer not comprising units with an LCST. The viscosity measurement is performed using a Haake RS150 rheometer equipped with a cone/plate geometry (35 mm, 2°) and a thermostatic bath so as to maintain the temperature between 5 and 80° C. The measurements were carried out in the flow mode at a shear rate of 10 s$^{-1}$, by varying the temperature from 15° C. to 50° C. at a rate of 0.5°/minute.

The following results are obtained:

| Polymer 1: | CAC = 0.9% by weight, |
|---|---|
| Polymer 2: | CAC = 0.3% by weight. |

EXAMPLE 1 Oil-in-water emulsion containing 20% (by weight) of parleam oil and 0.8% (by weight) of Polymer 2.

Emulsions are prepared from two-phase mixtures: aqueous solutions of polymer (1.6 g)/parleam oil (0.4 g), subjected to stirring using a DIAX 600 machine (Heidolph) for 5 minutes at 8000 rpm, and then for 1 minute at 13 500 rpm. The shaft used has an outside diameter of 10 mm (reference F10). The emulsification is performed in pill bottles with a volume of 10 ml.

The composition of the emulsions is as follows:

| Aqueous phase: | |
|---|---|
| Polymer 2 | 0.8 g |
| Demineralized water | 79.2 g |
| Oily phase: | |
| Parleam oil | 20 g |

The change in the macroscopic appearance of the emulsions is monitored over time, at 4° C. and at 45° C.; the stabilizing properties of the polymer are proportionately greater the greater the height of the emulsified phase.

At 4° C., at time t=0, 100% of the volume is emulsified. After 8 days, 50% of the volume is emulsified, and the aqueous phase is at the bottom of the pill bottle.

At 45° C., at time t=0, 100% of the volume is emulsified. After 20 days, 100% of the volume is emulsified, and the emulsion is thus stable.

Polymer 2 thus makes it possible to improve the stability of the emulsion at 45° C. when it is present in a low concentration by mass (0.8% by weight of the emulsion, i.e. 1% in aqueous phase).

FIG. 1 illustrates the change in the viscosity (in Pa.s) of an aqueous solution of Polymer 2 at 1% by weight in the temperature range from 4° C. to 45° C.

The rheological measurements were performed using a Haake RS 150 rheometer equipped with a cone/plate geometry (35 mm, 2°) and a thermostatic bath so as to maintain the temperature between 4° C. and 80° C. The measurements were carried out in the flow mode, at an imposed shear rate equal to $10\ s^{-1}$, by varying the temperature from 4° C. to 45° C. at a rate of 0.5° C./minute.

In FIG. 1, it is seen that the gel point of Polymer 2 at this concentration (1% by weight) is 27° C.

At a concentration of 2% by mass, the gel point of Polymer 2 is 29° C.

The gelling power of Polymer 2 above 27° C. thus makes it possible to improve the stability of the emulsion above this gel point, while at the same time maintaining a low viscosity at 20° C. (0.2 Pa.s under $10\ s^{-1}$). The texture of the composition at room temperature may thus be adjusted as desired by introducing a suitable gelling agent.

Comparative example: Oil-in-water emulsion containing 20% (by weight) of parleam oil and 0.29% of crosslinked poly(2-acrylamido-2-methylpropane sulphonic acid) (AMPS).

Emulsions are prepared from two-phase mixtures: aqueous solution of polymer (1.6 g)/parleam oil (0.4 g), subjected to stirring using a DIAX 600 machine (Heidolph) for 5 minutes at 8000 rpm and then for 1 minute at 13 500 rpm. The shaft used has an outside diameter of 10 mm (reference F10). The emulsification is performed in pill bottles with a volume of 10 ml.

The polymer solution is obtained by simple dissolution with stirring of the polymer in demineralized water in suitable proportions; the pH of this solution is then adjusted to 7 with 1M sodium hydroxide solution.

The composition of the emulsions is as follows:
Aqueous phase:

| Aqueous phase: | |
|---|---|
| Crosslinked poly(2-acrylamido-2-methylpropane sulphonic acid) | 0.29 g |
| Demineralized water | 79.71 g |
| Oily phase: | |
| Parleam oil | 20 g |

The macroscopic change in the emulsions obtained is monitored over time, at 4° C. and at 4520 C.

At 4° C., at time t=0, 100% of the volume is emulsified. After 6 days, 50% of the volume is emulsified, and the aqueous phase is at the bottom of the pill bottle.

At 45° C., 100% of the volume is emulsified at time t=0. After 6 days, 50% of the volume is emulsified, and the aqueous phase remains at the bottom of the pill bottle.

At 4° C. and at 45° C., this emulsion has the following viscosities (measured according to the protocol described in Example 1):

viscosity ($10\ s^{-1}$, 4° C.)=0.22 Pa.s
viscosity ($10\ s^{-1}$, 45° C.)=0.16 Pa.s This emulsion has a viscosity at 4° C. that is similar to that obtained for the solution of Polymer 2 in Example 1; the stabilities of the emulsions are similar at this temperature.

On the other hand, the emulsion becomes destabilized after 6 days at 45° C., unlike the emulsion of Example 1, the viscosity of the aqueous phase of which is higher (Emulsion 1: 1 Pa.s under 10 s-1 at 45° C.).

Thus, the polymer used in the invention makes it possible to stabilize the emulsion for 20 days, whereas the polymer used in this comparative example has no stabilizing power at 45° C.

EXAMPLE 2 Care cream

This cream has the following composition:

| Oily phase | |
|---|---|
| Parleam oil | 10% by weight |
| Polyethylene glycol-20 stearate (Myrj49 from Uniqema) | 0.7% by weight |
| Aqueous phase | |
| Polymer 1 | 4.5% by weight |
| $TiO_2$ particles (Luxelen SS from Sumitomo Seika Chemicals) | 5% by weight |
| Triethanolamine | 0.6% by weight |
| Preserving agent | 0.2% by weight |
| Demineralized water | 79% by weight |

The aqueous phase is prepared by simple mixing with stirring of an aqueous 10% suspension of $TiO_2$ and of an aqueous 10% solution of Polymer 1. The 10% $TiO_2$ suspension was prepared by adding, with stirring, $TiO_2$ particles to demineralized water containing the triethanolamine and the preserving agent. The final composition is obtained by slow introduction of the oily phase into the aqueous phase with stirring using a Moritz blender at a speed of 4000 rpm for 20 minutes.

The composition obtained is a cream that is stable after 30 days, above the gel point of Polymer 1, which is 25° C., at this concentration (4.5% by weight).

LIST OF REFERENCES CITED

[1] D. Hourdet et al., Polymer, 1994, Vol. 35, No. 12, pages 2624 to 2630;

[2] F. L'Alloret et al., Coll. Polym. Sci., 1995, Vol. 273, No. 12, pages 1163-1773;

[3] F. L'Alloret et al., Revue de l'Institut Françcais du Pétrole [Review of the French Petroleum Institute], 1997, Vol. 52, No. 2, pages 117-128;

[4] EP-A-0 583 814;
[5] EP-A-0 629 649;
[6] WO-A-95/24430;
[7] U.S. Pat. No. 5,939,584;
[8] WO-A-97/00275; and
[9] WO-A-98/48768.

The invention claimed is:

1. A dispersion in the form of a cosmetic make-up or care composition comprising at least one cosmetic or dermatological adjuvant, at least one aqueous phase and at least one oily phase, wherein the aqueous phase comprises a polymer comprising water-soluble units and units with an LCST, the units with an LCST having in water a demixing temperature of from 5 to 40° C. at a concentration of 1% by mass, and the polymer being present in the aqueous phase at a concentration such that the gel point of the aqueous phase is from 5 to 40° C., to ensure the stability of the dispersion when it is subjected to temperature variations in the range from 4 to 50° C., wherein the polymer comprises an oligomer or copolymer of water-soluble units wherein the polymer is water-soluble at all temperatures from 5 to 80° C. at a concentration of at least 10 g/l, and wherein the units with an LCST are one or more of the following polymers:

polyethers; polyvinyl methyl ethers; polymeric N-substituted acrylamide derivatives;

copolymers of N-isopropylacrylamide or of N-ethylacrylaide and a vinyl monomer corresponding to formula (I):

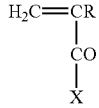
(I)

wherein:
R is from H,—CH$_3$,—C$_2$H$_5$ or —C$_3$H$_7$, and
X is:
OR' alkyl oxides wherein R' is a linear or branched, saturated or unsaturated hydrocarbon radical containing from 1 to 6 carbon atoms, optionally substituted with at least one halogen atom; a sulphonic group, a sulphate group, a phosphate group; a hydroxyl group; a primary amine; a secondary amine; a tertiary amine; or a quaternary amine group of the formula N$^+$R$_1$R$_2$R$_3$ wherein R$_1$, R$_2$ and R$_3$ are, independently, a linear or branched, saturated or unsaturated hydrocarbon radical containing 1 to 6 carbon atoms, with the proviso that the sum of the carbon atoms of R'+R$_1$+R$_2$+R$_3$ does not exceed 7; and —NH$_2$,—NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$+R$_5$ does not exceed 7, the said R$_4$ and R$_5$ optionally being substituted with a halogen atom (iodine, bromine, chlorine or fluorine); a hydroxyl (—OH); sulphonic (—SO$_3^-$), sulphate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$+R$_2$+R$_3$ does not exceed 7;

copolymers of N-isopropylacrylamide or of N-ethylacrylaide and a monomer selected from the group consisting of maleic anhydride, itaconic acid, vinylpyrrolidone, styrene and its derivatives, dimethyldiallylammonium chloride, vinylacetamide, vinyl ethers and vinyl acetate derivatives; or polyvinylcaprolactam; copolymers of vinylcaprolactam and a vinyl monomer corresponding to formula (I).

2. The dispersion as claimed in claim 1, formed by an oil-in-water emulsion in which water is the aqueous phase.

3. The dispersion as claimed in claim 1, formed by a dispersion of mineral and/or organic particles in the aqueous phase of an oil-in-water emulsion.

4. The dispersion as claimed in claim 1, in which the polymer is in the form of a block polymer comprising water-soluble units alternating with units with an LCST, or in the form of a grafted polymer whose backbone is formed from water-soluble units and bears grafts consisting of units with an LCST.

5. The dispersion as claimed in claim 1, in which the water-soluble units are obtained by free-radical polymerization of at least one monomer selected from the group consisting of:
(meth)acrylic acid;
vinyl monomers of formula (I) below:

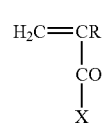
(I)

in which:
R is H,—CH$_3$,—C$_2$H$_5$ or —C$_3$H$_7$, and
X is:
alkyl oxides of —OR' type in which R' is a linear or branched, saturated or unsaturated hydrocarbon radical containing from 1 to 6 carbon atoms, optionally substituted with at least one halogen atom selected from the group consisting of iodine, bromine, chlorine and fluorine; a sulfonic (—SO$_3^-$), sulfate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R'+R$_1$+R$_2$+R$_3$ does not exceed 7; and —NH$_2$,—NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$+R$_5$ does not exceed 7, the said R$_4$ and R$_5$ optionally being substituted with a halogen atom selected from the group consisting of iodine, bromine, chlorine and fluorine; a hydroxyl (—OH); sulfonic (—SO$_3^-$), sulfate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$+R$_2$+R$_3$ does not exceed 7;

maleic anhydride;
itaconic acid;
vinyl alcohol of formula CH$_2$=CHOH;
vinyl acetate of formula CH$_2$=CH—OCOCH$_3$;
N-vinyllactams;
vinyl ethers of formula CH$_2$=CHOR$_6$ in which R$_6$ is a linear or branched, saturated or unsaturated hydrocarbon radical containing from 1 to 6 carbons atoms;
water-soluble styrene derivatives;
dimethyldiallylammonium chloride; and
vinylacetamide.

6. The dispersion as claimed in claim 1, in which the water-soluble units have a molar mass ranging from 1000 g/mol to 5 000 000 g/mol when they constitute the water-soluble backbone of a grafted polymer, or a molar mass ranging from 500 g/mol to 100 000 g/mol when they constitute a block of a multiblock polymer or when they constitute the grafts of a grafted polymer.

7. The dispersion as claimed in claim 1, in which the units with an LCST are one or more of the following polymers:
polyethers,
polyvinyl methyl ethers,
polymeric and copolymeric N-substituted acrylamide derivatives with an LCST and
polyvinylcaprolactam and vinylcaprolactam copolymers.

8. The dispersion as claimed in claim 7, in which the units with an LCST are polymeric or copolymeric N-isopropylacrylamide or N-ethylacrylamide derivatives and the molar mass of these units with an LCST is from 1000 g/mol to 50 000 g/mol.

9. The dispersion as claimed in claim 1, in which the proportion by mass of units with an LCST in the polymer is from 5 to 70% relative to the polymer.

10. The dispersion as claimed in claim 1, in which the demixing temperature of the units with an LCST is from 10 to 35° C., for a concentration in water of 1% by mass of the units with an LCST.

11. The dispersion as claimed in claim 1, in which the concentration by mass of polymer in the aqueous phase is from 0.01 to 20%.

12. The dispersion as claimed in claim 1, in which the polymer is such that an aqueous solution of this polymer at 2% by weight has a gel point of from 5 to 40° C.

13. The dispersion as claimed in claim 1, in which the oily phase comprises at least one oil selected from the group consisting of hydrocarbon-based animal oils, hydrocarbon-based plant oils, synthetic esters, synthetic ethers, linear hydrocarbons, branched hydrocarbons, essential oils, fatty alcohols, fluoro oils, silicone oils, and mixtures thereof 14. The dispersion as claimed in claim 1, wherein the polymer is in the form of a block polymer in the form of a grafted polymer whose backbone is formed from water-soluble units and bears grafts consisting of units with an LCST and which is partially crosslinked.

15. The dispersion as claimed in claim 7, wherein at least one polymer is polymeric and copolymeric N-substituted acrylamide derivatives with an LCST and is one or more of poly-N-isopropyl acrylamide, poly-N-ethylacrylamide and copolymers of N-isopropylacrylamide or of N-ethylacrylamide and of a vinyl monomer corresponding to formula (I)

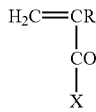

in which:
R is chosen from H, —CH$_3$, —C$_2$H$_5$ or —C$_3$H$_7$, and
X is chosen from:
alkyl oxides of -OR' type in which R' is a linear or branched, saturated or unsaturated hydrocarbon radical containing from 1 to 6 carbon atoms, optionally substituted with at least one halogen atom selected from the group consisting of iodine, bromine, chlorine, and fluorine; a sulfonic (—SO$_3^-$), sulfate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R'+R$_1$+R$_2$+R$_3$ does not exceed 7; and
—NH$_2$, —NHR$_4$ and —NR$_4$R$_5$ groups in which R$_4$ and R$_5$ are, independently of each other, linear or branched, saturated or unsaturated hydrocarbon radicals containing 1 to 6 carbon atoms, with the proviso that the total number of carbon atoms in R$_4$+R$_5$ does not exceed 7, the said R$_4$ and R$_5$ optionally being substituted with a halogen atom selected from the group consisting of iodine, bromine, chlorine and fluorine; a hydroxyl (—OH); sulfonic (—SO$_3^-$), sulfate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$+R$_2$+R$_3$ does not exceed 7;
or of a monomer chosen from maleic anhydride, itaconic acid, vinylpyrrolidone, styrene and its derivatives, dimethyldiallylammonium chloride, vinylacetamide, vinyl ethers and vinyl acetate derivatives.

16. The dispersion as claimed in claim 1, wherein the one or more adjuvants are selected from the group consisting of mineral fillers, organic fillers, surfactants, hydrophilic active agents, lipophilic active agents, preserving agents, gelling agents, plasticizers, antioxidants, fragrances, odor absorbers, antifoams, sequestering agents, pH adjusters, buffers and dyestuffs.

17. The dispersion as claimed in claim 8, wherein the molar mass of the units with an LCST is from 200 to 50 000 g/mol.

18. The dispersion as claimed in claim 9, wherein the proportion by mass of units with an LCST in the polymer is from 20 to 65% relative to the polymer.

19. The dispersion as claimed in claim 9, wherein the proportion by mass of units with an LCST in the polymer is from 30 to 60% relative to the polymer.

20. The dispersion as claimed in claim 11, wherein the concentration by mass of polymer in the aqueous phase is from 0.1 to 10%.

21. The dispersion as claimed in claim 12, wherein the polymer is such that an aqueous solution of this polymer at 2% by weight has a gel point of from 10 to 35° C.

22. The dispersion as claimed in claim 5, wherein the water-soluble units are (meth)acrylic acid.

23. The dispersion as claimed in claim 7, wherein the units with an LCST are polymeric and copolymeric N-substituted acrylamide derivatives with an LCST.

* * * * *